(12) United States Patent
Masuyama et al.

(10) Patent No.: US 9,339,537 B2
(45) Date of Patent: May 17, 2016

(54) CANCER INHIBITING AGENT, ANTIBODY PRODUCTION ENHANCING AGENT, AND THERAPEUTIC AGENT FOR HEPATITIS

(75) Inventors: Junichi Masuyama, Oyama (JP); Sanehiko Fujita, Tokyo (JP)

(73) Assignees: Cellex Corporation, Tokyo (JP); Junichi Masuyama, Tochigi (JP); Sanehiko Fujita, Tokyo (JP)

( * ) Notice: Subject to any disclaimer, the term of this patent is extended or adjusted under 35 U.S.C. 154(b) by 1 day.

(21) Appl. No.: 14/002,395

(22) PCT Filed: Mar. 2, 2011

(86) PCT No.: PCT/JP2011/054663
§ 371 (c)(1),
(2), (4) Date: Oct. 7, 2013

(87) PCT Pub. No.: WO2012/117532
PCT Pub. Date: Sep. 7, 2012

(65) Prior Publication Data
US 2014/0023682 A1    Jan. 23, 2014

(51) Int. Cl.
*A61K 35/17* (2015.01)
*A61K 39/29* (2006.01)
*A61K 39/12* (2006.01)

(52) U.S. Cl.
CPC .............. *A61K 39/292* (2013.01); *A61K 35/17* (2013.01); *A61K 39/12* (2013.01); *C12N 2730/10134* (2013.01)

(58) Field of Classification Search
None
See application file for complete search history.

(56) References Cited

U.S. PATENT DOCUMENTS

| 2011/0165194 A1* | 7/2011 | Yum et al. ................... 424/227.1 |
| 2012/0093792 A1 | 4/2012 | Masuyama |
| 2013/0011376 A1* | 1/2013 | Peled et al. ................. 424/93.71 |

FOREIGN PATENT DOCUMENTS

| JP | 2001-314183 | 11/2001 |
| JP | 2011-1315 | 1/2011 |
| JP | 5016732 | 6/2012 |

OTHER PUBLICATIONS

Albarran et al. (APMIS, 2005, p. 526-535).*
International Preliminary Report on Patentability issued in corresponding International Patent Application No. PCT/JP2011/054663 dated Sep. 3, 2013 (13 pages).
Yang et al., "Effect of Low Dose Radiation (LDR) on Biological Activity of NK Cell," Fangshe Mianyixue Zazhi, 2006, vol. 19, No. 6, pp. 529-535 (Abstract only, 2 pages).
Matsumoto et al., "A Case in Which a Large Amount of NK Cells were Administered for Relapse After Liver Cancer Surgery, Allowing a Long-Term Follow-Up," Department of Digestive Organs and Internal Medicine, Nihon University: Department of Digestive Organs, Yokohama Central Hospital: New City Osaki Clinic, Sep. 15, 2007, No. 48, Suppl. 2, p. A451 (pp. 1-3).
Raulet et al., "Oncogenic stress sensed by the immune system: role of natural killer cell receptors," Nature Reviews, Immunology, Aug. 2009, vol. 9, pp. 568-580.
Whiteside et al., "The role of natural killer cells in immune surveillance of cancer," Current Opinion in Immunology, Oct. 1995, vol. 7, No. 5, pp. 704-710.
Imai et al., "Natural cytotoxic activity of peripheral-blood lymphocytes and cancer incidence: an 11-year follow-up study of a general population," The Lancet, vol. 356, No. 9244, Nov. 25, 2000, pp. 1795-1799.
Masuyama et al., "NK Saibo Tairyo Toyo C-gata Kan'en Virus o Seigyo Dekiruka", The Journal of Therapy, vol. 88, No. 7, Jul. 2006, pp. 2028-2032 (11 pages).
Yoshida et al., "Control of liver dendritic cells and acquired immunity by Liver Natural killer cell," Journal of Gastroenterology and Hepatology, May 25, 2007, No. 43, pp. 7-9 (Abstract only, 1 page).
Chen et al., "Impaired function of hepatic natural killer cells from murine chronic HBsAg carriers," International Immunopharmacology, Dec. 2005, vol. 5, No. 13-14, pp. 1839-1852.
Partial Translations of Notifications of Reasons for Refusal issued in corresponding Japanese Patent No. 5016732.

* cited by examiner

*Primary Examiner* — Agnieszka Boesen
(74) *Attorney, Agent, or Firm* — Kilyk & Bowersox, P.L.L.C.

(57) ABSTRACT

Provided are an agent for inhibition of cancer development, an agent for improvement of antibody productivity, and an agent for treatment of hepatitis. The agents have been completed by finding that cancer development is inhibited in a healthy subject by administering NK cells, and antibody productivity is improved by administering NK cells and a vaccine to a patient.

4 Claims, 11 Drawing Sheets

PROFILES OF ADMINISTRATION GROUP
SUBJECT WITH CANCER DEVELOPMENT IS UNDERLINED.
PRESERVATION PERIODS REFER TO PERIODS TO CANCER DEVELOPMENT.

| ID number | AGE | SEX | PRESERVATION PERIOD (MONTHS) | ID number | AGE | SEX | PRESERVATION PERIOD (MONTHS) |
|---|---|---|---|---|---|---|---|
| A1 | 55 | M | 60 | A32 | 52 | M | 32 |
| A2 | 62 | M | 60 | A33 | 56 | M | 30 |
| A3 | 61 | F | 60 | A34 | 52 | F | 29 |
| A4 | 60 | M | 60 | A35 | 70 | M | 28 |
| A5 | 56 | F | 60 | A36 | 58 | F | 28 |
| A6 | 63 | F | 60 | A37 | 39 | M | 23 |
| A7 | 46 | M | 60 | A38 | 61 | M | 22 |
| A8 | 69 | M | 59 | A39 | 58 | F | 21 |
| A9 | 65 | M | 59 | A40 | 60 | M | 21 |
| A10 | 73 | M | 59 | A41 | 61 | M | 21 |
| A11 | 67 | M | 59 | A42 | 65 | F | 21 |
| A12 | 48 | M | 59 | A43 | 73 | F | 21 |
| A13 | 72 | M | 58 | A44 | 69 | M | 21 |
| A14 | 60 | M | 58 | A45 | 56 | F | 21 |
| A15 | 53 | M | 58 | A46 | 63 | M | 20 |
| A16 | 57 | F | 57 | A47 | 58 | F | 18 |
| A17 | 53 | F | 57 | A48 | 73 | M | 17 |
| A18 | 65 | F | 57 | A49 | 72 | F | 17 |
| A19 | 62 | F | 57 | A50 | 67 | F | 16 |
| A20 | 58 | F | 56 | A51 | 67 | M | 15 |
| A21 | 56 | M | 56 | A52 | 53 | M | 13 |
| A22 | 55 | F | 52 | A53 | 68 | F | 13 |
| A23 | 64 | F | 51 | | | | |
| A24 | 66 | M | 51 | | | | |
| A25 | 70 | M | 50 | | | | |
| A26 | 71 | M | 50 | | | | |
| A27 | 60 | M | 49 | | | | |
| A28 | 73 | M | 47 | | | | |
| A29 | 51 | F | 39 | | | | |
| <u>A30</u> | <u>57</u> | <u>F</u> | <u>34</u> | | | | |
| A31 | 56 | M | 33 | | | | |

Fig. 6

PROFILES OF NON-ADMINISTRATION GROUP
SUBJECT WITH CANCER DEVELOPMENT ARE UNDERLINED.
PRESERVATION PERIODS REFER TO PERIODS TO CANCER DEVELOPMENT.

| ID number | AGE | SEX | PRESERVATION PERIOD (MONTHS) | ID number | AGE | SEX | PRESERVATION PERIOD (MONTHS) |
|---|---|---|---|---|---|---|---|
| _B1_ | _68_ | _M_ | _8_ | B31 | 63 | M | 50 |
| B2 | 62 | F | 60 | B32 | 63 | F | 49 |
| B3 | 66 | F | 60 | B33 | 65 | F | 49 |
| B4 | 54 | M | 59 | B34 | 64 | M | 47 |
| B5 | 52 | F | 59 | _B35_ | _70_ | _F_ | _34_ |
| B6 | 66 | M | 59 | B36 | 68 | F | 46 |
| B7 | 44 | F | 59 | B37 | 59 | M | 46 |
| B8 | 65 | M | 59 | B38 | 53 | F | 44 |
| _B9_ | _49_ | _M_ | _58_ | B39 | 63 | M | 44 |
| _B10_ | _42_ | _M_ | _53_ | B40 | 67 | M | 44 |
| B11 | 41 | F | 59 | B41 | 57 | M | 43 |
| B12 | 67 | M | 59 | B42 | 56 | F | 43 |
| B13 | 61 | F | 59 | B43 | 73 | F | 34 |
| B14 | 44 | F | 59 | B44 | 55 | M | 32 |
| B15 | 66 | M | 59 | B45 | 54 | M | 31 |
| B16 | 53 | F | 59 | _B46_ | _58_ | _F_ | _5_ |
| B17 | 43 | F | 59 | B47 | 69 | M | 21 |
| B18 | 40 | F | 58 | B48 | 74 | F | 19 |
| B19 | 69 | M | 58 | B49 | 59 | F | 18 |
| B20 | 64 | F | 58 | B50 | 65 | M | 13 |
| B21 | 64 | M | 58 | | | | |
| B22 | 63 | F | 58 | | | | |
| B23 | 71 | M | 58 | | | | |
| B24 | 60 | M | 57 | | | | |
| B25 | 58 | F | 57 | | | | |
| B26 | 59 | M | 56 | | | | |
| _B27_ | _65_ | _M_ | _49_ | | | | |
| _B28_ | _71_ | _M_ | _2_ | | | | |
| B29 | 63 | F | 51 | | | | |
| B30 | 63 | F | 51 | | | | |

CANCER INHIBITING AGENT, ANTIBODY PRODUCTION ENHANCING AGENT, AND THERAPEUTIC AGENT FOR HEPATITIS

The present application is a National Stage Application of PCT/JP2011/054663, filed Mar. 2, 2011.

TECHNICAL FIELD

The present invention relates to an agent for inhibition of cancer development including a natural killer (hereinafter referred to as NK) cell as an active ingredient, an agent for improvement of antibody productivity including an NK cell as an active ingredient, an agent for treatment of hepatitis including a combination of an NK cell as an active ingredient and a hepatitis vaccine as an active ingredient, a method for inhibition of cancer development including the step of administering an NK cell, a method for improvement of antibody productivity including the step of administering an NK cell and a vaccine, and a method for treatment of hepatitis including the step of administering an NK cell and a hepatitis vaccine.

BACKGROUND ART (With Regard to Cancer Prevention)

Since cancer became a major cause of death, various attempts have been made to elucidate risk factors and inhibitory factors for cancer development so as to utilize these factors in cancer prevention through elimination or ingestion thereof, as well as to develop drugs for treatment of cancer. As typical examples of the risk factors for cancer development, there are known a lifestyle such as smoking, and persistent infection with a hepatitis virus (hepatoma), a parvovirus (cervical cancer), *Helicobacter pylori* (gastric cancer), or the like. As an example of the utilization of the elimination of the risk factors in cancer prevention, there is given a preventive vaccine therapy for blocking infection with a hepatitis B virus and a parvovirus.

On the other hand, for the inhibitory factors, large-scale epidemiological investigations have been performed on foods. Further, in drugs, it has been reported that a non-steroidal anti-inflammatory drug for large bowel cancer or a selective estrogen receptor modulator (SERM) for breast cancer reduces a risk of cancer development.

Possible mechanisms of cancer prevention with the foods or the drugs are proliferation inhibition of cancer cells, apoptosis induction, modification of a hormone receptor, an increase in immune sensitivity of cancer cells, and the like.

A concept of such cancer prevention is based on the following perspective: how to inhibit factors on the cancer cell side, such as transformation from normal cells to cancer cells and proliferation and metastasis of cancer cells. On the other hand, it is also theoretically possible to inhibit cancer development by enhancing factors on the living body side for protecting against the cancer development, that is, immune surveillance abilities as described below from a tumor immunological viewpoint.

(With Regard to Immune System)

In the middle of the 20th century, Burnet proposed, based on experiments using mice, the presence of an immune surveillance mechanism in which precancerous cells were recognized and eliminated by the immune system to block their progression to cancer, thereby maintaining homeostasis of an individual. After that, evidence of the presence of the immune surveillance mechanism was demonstrated by development of genetically-modified mouse models, and complicated associations and processes between the cancer development and the immune system were organized in the immunoediting theory by Dunn et al. (Non Patent Literature 1: Nat. Immunl. 2002; 3: 991).

According to the immunoediting theory, the processes to cancer development are divided into three stages, i.e., elimination, equilibrium, and escape. In particular, the first stage, i.e., elimination has substantially the same meaning as the immune surveillance theory, and is a process in which initial cancer cells are eliminated before formation of a large population. In the first half of this process, NK cells, NKT cells, γδT cells, macrophages, and dendritic cells as innate immune cells function in cooperation with each other to eliminate tumor cells. In the second half, the dendritic cells present cancer antigens to T cells to produce clones of cancer antigen-specific helper T cells and cytotoxic T cells, and acquired immunity functions so as to eliminate cancer cells that have not been able to be eliminated by innate immunity alone.

At the second stage, i.e., equilibrium, selection of cancer cells having low immunogenicity progresses even in a living body retaining normal immune functions. Finally, the cancer cells acquire immune resistance, and proliferation of the cancer cells gradually occurs.

The third stage, i.e., escape is a stage at which the immune system cannot recognize cancer cells any more, which causes a rapid increase in cancer tissue, with the result that cancer is clinically detectable.

As the stage becomes more advanced from the equilibrium, it becomes more difficult to inhibit progression of cancer. Hence, in order to inhibit cancer development, it is essential to certainly eliminate cancer cells at the first stage, i.e., elimination. However, functions of innate immune cells and acquired immune cells are reduced by aging, stress, and the like, with the result that their abilities to eliminate cancer cells are not sufficiently exhibited. For example, although cytotoxicity and interferon-γ productivity of NK cells are also attenuated by aging, there is a report that functions of NK cells and NKT cells in the innate immune system are kept high in immune abilities of centenarians (Non Patent Literature 2: J. Clin. Immunol. 2009; 29: 416).

(Means for Inhibiting Cancer Development)

The previously reported means for inhibiting cancer development are limited to a food, a supplement (e.g., selenium or a vitamin), an anti-inflammatory drug, and a selective estrogen receptor modulator (SERM), all of which directly act on cancer cells to inhibit their progression, and the inhibiting effects are not necessarily high. Further, as a countermeasure for attenuation of a vaccine effect by aging and the like, it is only possible to increase a single dosage of a vaccine adjuvant or a vaccine or the number of times of administration.

(With Regard to Hepatitis)

In the world, there are 360,000,000 chronic hepatitis patients infected with a hepatitis B virus who are at risk of developing liver cirrhosis and hepatoma. This has become a big issue. Although attempts to use a hepatitis B vaccine for preventive uses as a vaccine for "treatment" of chronic hepatitis B in combination with a virus proliferation inhibitor were made, no satisfactory clinical improvement was found (Non Patent Literature 3: Vaccine 2007; 25: 8585 and Non Patent Literature 4: Hepat. Res. Treat. 2010; 2010: 817580).

In addition, development of a "treatment" vaccine therapy has also been explored, such as a clinical trial on a novel DNA vaccine (Non Patent Literature 5: Gene Ther. 2006; 13: 1110) or immune complex vaccine (Non Patent Literature 6: PLoS One 2008; 3: e2565).

However, the presence of a population (e.g., males aged 60 or more) showing no or very little increase in antibody titer even when a general HB vaccine is administered has become an issue.

In addition, interferon to be generally used in treatment of hepatitis exhibits different therapeutic effects depending on patients. Thus, there is a need for establishment of a novel treatment method.

(With Regard to Agent for Improvement of Antibody Production)

There are reports on agents for improvement of antibody production.

In Patent Literature 1, there is a disclosure of an "agent for induction of antibody production, including a tea polysaccharide as an active ingredient."

In Patent Literature 2, there is a disclosure of an "agent for improvement of antibody productivity of a vaccine, characterized by containing egg white."

However, none of the literatures discloses or suggests an "agent for improvement of antibody production, including NK cells." In addition, there are many reports that the NK cells inhibit antibody productivity (Non Patent Literature 7: Cell. Immunol. 1995; 161: 42). That is, in the conventional findings, it has generally been recognized that the NK cells inhibit antibody productivity.

CITATION LIST

Patent Literature

[PTL 1] JP 2006-340698 A
[PTL 2] JP 05-124972 A

Non Patent Literature

[NPL 1] Nat. Immunl. 2002; 3: 991
[NPL 2] J. Clin. Immunol. 2009; 29: 416
[NPL 3] Vaccine 2007; 25: 8585
[NPL 4] Hepat. Res. Treat. 2010; 2010: 817580
[NPL 5] Gene Ther. 2006; 13: 1110
[NPL 6] PLoS One 2008; 3: e2565
[NPL 7] Cell. Immunol. 1995; 161: 42

SUMMARY OF INVENTION

Technical Problem

Various immune cells such as NK cells, NKT cells, γδT cells, macrophages, dendritic cells, and T cells are involved in the elimination process for cancer cells. However, it is unknown which immune cells play a major role in eliminating cancer cells.

Thus, the inventors have considered that "when the major immunocompetent cells are revealed, artificial enhancement of their functions can improve immune surveillance abilities, thereby re-strengthening the elimination process, and the re-strengthening is expected to finally lead to a reduction in rate of cancer development as compared to the case where the re-strengthening is not performed."

In addition, based on the finding that "it has been pointed out that, even in the above-mentioned vaccine therapy, similarly to cancer development, aging causes reductions in functions of NK cells and dendritic cells and decreases in numbers of naive T cells and B cells, resulting in reductions in immune reactivity against foreign antigens, and in actuality, in some of healthy subjects, HIV positive patients, dialysis patients, and alcoholism patients, a hepatitis B vaccine induces no antibody and shows no or low reactivity," the inventors have considered that such no or low reactivity finally results in increased risks of chronic hepatitis and hepatoma.

In addition, the inventors of the present invention have considered as follows: "a vaccine effect is induced by enhancing again the reduced immune reactivity as a cause for no or low reactivity, which can finally lead to prevention of cancer, in particular, hepatoma."

Thus, based on the above-mentioned findings, the inventors of the present invention aim to provide an agent for inhibition of cancer development, an agent for improvement of antibody productivity, and an agent for treatment of hepatitis.

Solution to Problem

The inventors of the present invention have made extensive studies in order to solve the above-mentioned problems. As a result, the inventors have found that cancer development is inhibited by administering NK cells, and antibody productivity is improved by administering NK cells and a vaccine to a patient. Thus, the present invention has been completed.

That is, the present invention is as described below.

"1. An agent for inhibition of cancer development in a healthy subject, including an NK cell as an active ingredient.

2. An agent for inhibition of cancer development in a healthy subject according to the above-mentioned item 1, in which the NK cell includes an activated NK cell.

3. A method for inhibition of cancer development in a healthy subject, including administering an activated NK cell to a healthy subject.

4. A method for inhibition of cancer development according to the above-mentioned item 3, in which the activated NK cell includes an NK cell derived from the healthy subject.

5. An agent for improvement of antibody productivity of a vaccine, including an NK cell as an active ingredient.

6. An agent for improvement of antibody productivity according to the above-mentioned item 5, in which the vaccine includes a hepatitis vaccine.

7. An agent for improvement of antibody productivity according to the above-mentioned item 6, in which the hepatitis vaccine includes a hepatitis B vaccine.

8. An agent for improvement of antibody productivity according to any one of the above-mentioned items 5 to 7, in which the NK cell includes an activated NK cell.

9. An agent for treatment of hepatitis, including a combination of an NK cell as an active ingredient and a hepatitis vaccine as an active ingredient.

10. An agent for treatment of hepatitis according to the above-mentioned item 9, in which the hepatitis vaccine includes a hepatitis B vaccine.

11. A kit for treatment of hepatitis, including an agent for improvement of antibody productivity of a vaccine, containing an NK cell as an active ingredient, and a hepatitis vaccine.

12. A kit for treatment of hepatitis according to the above-mentioned item 11, in which the hepatitis vaccine includes a hepatitis B vaccine.

13. A method for improvement of antibody productivity of a vaccine in a patient, including the following steps (1) and (2) or (1)' and (2)':

(1) a step of administering an activated NK cell to a patient; and
(2) a step of administering a vaccine to the patient; or
(1)' a step of administering a vaccine to a patient; and
(2)' a step of administering an activated NK cell to the patient.

14. A method for improvement of antibody productivity according to the above-mentioned item 13, in which the activated NK cell includes an NK cell derived from the patient.

15. A method for improvement of antibody productivity according to the above-mentioned item 13 or 14, in which the vaccine includes a hepatitis vaccine.

16. A method for improvement of antibody productivity according to the above-mentioned item 15, in which the hepatitis vaccine includes a hepatitis B vaccine.

17. A method for treatment of hepatitis, including the following steps (1) and (2) or (1)' and (2)':
(1) a step of administering an activated NK cell to a patient; and
(2) a step of administering a vaccine to the patient; or
(1)' a step of administering a vaccine to a patient; and
(2)' a step of administering an activated NK cell to the patient.

18. A method for treatment of hepatitis according to the above-mentioned item 17, in which the activated NK cell includes an NK cell derived from the patient.

19. A method for treatment of hepatitis according to the above-mentioned item 17 or 18, in which the hepatitis includes hepatitis B."

Advantageous Effects of Invention

Cancer development in a healthy subject was inhibited by the agent for inhibition of cancer development and method for inhibition of cancer development of the present invention. In addition, even in a case where an increase in antibody titer is hardly achieved by a vaccine alone, the increase in antibody titer was able to be achieved by the agent for improvement of antibody productivity and method for improvement of antibody productivity of the present invention.

DESCRIPTION OF EMBODIMENTS (NK Cells)

Any NK cells acquired by a method known per se may be utilized as NK cells to be used in the present invention. However, activated NK cells are preferably used.

It should be noted that an NK cell donor and an NK cell recipient are preferably the same species. For example, when the donor is a human, the recipient is a human.

Further, the NK cell donor and the NK cell recipient are more preferably the same individual. For example, when the donor is a donor X, the recipient is the donor X.

(Method for Acquisition of NK Cells)

The NK cells to be used in the present invention may be acquired by a method known per se (see: Table 1). The NK cells are acquired by induction from mononuclear cells collected from peripheral blood, lymph nodes, thymus, bone marrow, tumors, pleural effusion, ascites, or umbilical cord blood, more preferably peripheral blood mononuclear cells.

For example, the mononuclear cells containing the NK cells may be collected from peripheral blood by a specific gravity centrifugation method. Further, for example, the NK cells may be isolated by a cell sorter, panning, an antibody magnetic bead method, or the like using an antibody against a cell surface marker specifically expressed on the NK cells.

TABLE 1

Method for culture and proliferation of NK cells

| Study | Start material | Stimulation | Feeder cells | NK cell isolation | Serum | Medium | NK fold expansion/time | References |
|---|---|---|---|---|---|---|---|---|
| Alici | PBMC | Anti-CD3 | No | No | Human AB serum | CellGro SCGM | x190/3w | Hum Immunol 2001; 62: 1092 |
| Campana | PBMC | 4-1BB&IL-15 gene-transfected K562 | K562 | No | Feral bovine serum | CellGro SCGM | x152/2w | Cancer Res 2009; 69: 4010 |
| Childs | PBMC | No | EBV-TM B-cell line | Yes | Human AB serum | X-VIVO 20 | x300-900/19d | Cytotherapy 2009; 11: 341 |
| Multhoff | PBMC | Hsp-70-peptide | No | No | No | CellGro SCGM | $0.9\text{-}1.9 \times 10^9$ | J Transl Med 2009; 7: 50 |
| Dolstra | Umbical cord CD34+ | SCF, IL7, Flt3L, TPO, G-CSF, GM-CSF, IL-6, MIP-1a, LIF | No | No | No | GBGM | x1500-6500/5w ($4.6 \pm 2.4 \times 10^9$) | PlosONE 2010; 5: e9221 |

(Method for Activation of NK Cells)

In a method for activation of NK cells of the present invention, mononuclear cells containing T cells and NK cells can be stimulated with a CD3 agonist and a CD52 agonist to activate the NK cells more than the T cells, and the NK cells can be proliferated safely and simply without being mixed with K562 and the like. Particularly when the mononuclear cells containing T cells and NK cells are stimulated with the CD3 agonist and the CD52 agonist in the presence of IL-2, the NK cells can be more proliferated than the T cells as compared to stimulation with IL-2 alone. Further, the use of the method for activation of NK cells of the present invention allows the NK cells to be proliferated 1,000 times or more (see: JP 2005-124568 A).

(Agent for Inhibition of Cancer Development in Healthy Subject)

An agent for inhibition of cancer development in a healthy subject of the present invention contains at least NK cells, preferably activated NK cells as an active ingredient, and it is more preferred that the content of the activated NK cells be the largest among all the cells.

Further, the agent for inhibition of cancer development of the present invention may contain cells except the NK cells, for example, immune cells such as NKT cells, T cells, dendritic cells, and γδT cells. In addition, the agent for inhibition of cancer development of the present invention may contain NK cells as a mixture with an active ingredient for any other treatment.

The agent for inhibition of cancer development of the present invention is manufactured by mixing an effective amount of an active ingredient together with one or more kinds of pharmacologically acceptable carriers, and employing any method well known in the art of pharmaceutics. Various substances are known as the pharmacologically acceptable carriers, and one appropriately selected from the substances is used. Examples thereof may include buffers and various additives such as salts, serum, albumin, and amino acids.

It should be noted that the term "healthy subject" as used herein means a mammal that has not been diagnosed to have cancer in a variety of inspection and diagnosis, and also encompasses a mammal that has a disease except cancer. In addition, the term also encompasses a mammal that does not need to be treated at present in consideration of sizes of cancer cells and tumors.

The agent for inhibition of cancer development in a healthy subject of the present invention is generally provided in dosage forms such as injections and drops. The agent for inhibition of cancer development in a healthy subject of the present invention is preferably a suspension in which the activated NK cells are suspended in a sterile aqueous carrier isotonic to body fluid (such as blood) of a recipient. Examples of the aqueous carrier may include physiological saline and phosphate-buffered physiological saline (PBS). Such aqueous carrier may be further supplemented with a solubilizing aid, a buffer, a tonicity agent, a soothing agent, a preservative, a stabilizer, or the like as necessary.

The concentration of the NK cells and/or activated NK cells contained in the agent for inhibition of cancer development in a healthy subject of the present invention falls within the range of generally about $1\times10^5$ to $1\times10^{11}$ cells/ml, preferably about $1\times10^6$ to $1\times10^{10}$ cells/ml, but is not particularly limited. When the cell concentration is too low, it takes long time for administration, resulting in an increased burden on a patient. When the cell concentration is too high, aggregation may occur between the cells.

(Method for Inhibition of Cancer Development)

A method for inhibition of cancer development of the present invention includes administering NK cells, preferably activated NK cells to a healthy subject It should be noted that the NK cells do not need to be NK cells derived from the healthy subject. However, the method preferably includes at least the following steps.

(1) a step of proliferating and activating NK cells acquired from a healthy subject
(2) a step of administering the activated NK cells to the healthy subject Further, the NK cells are preferably administered to a blood vessel of a human body by injection, infusion, or the like.

The administration of the NK cells or the activated NK cells includes administering $10^2$ to $10^{12}$ cells per administration. The administration is repeated 1 to 12 times a year, and is preferably performed once or twice.

More specifically, the dosage of the NK cells or the activated NK cells varies depending on an administration form, the age and body weight of a patient, and the like. In general, however, the cells are administered at a dose of generally $1\times10^7$ to $1\times10^{11}$ cells, preferably $1\times10^8$ to $1\times10^{10}$ cells in terms of the number of activated NK cells per administration.

(Agent for Improvement of Antibody Productivity of Vaccine)

An agent for improvement of antibody productivity of a vaccine of the present invention contains at least NK cells, preferably activated NK cells as an active ingredient, and it is more preferred that the content of the activated NK cells be largest among all the cells.

Further, the agent for improvement of antibody productivity of a vaccine of the present invention may contain cells except the NK cells, for example, immune cells such as NKT cells, T cells, dendritic cells, and γδT cells. In addition, the agent for improvement of antibody productivity of a vaccine of the present invention may contain NK cells as a mixture with an active ingredient for any other treatment.

The agent for improvement of antibody productivity of a vaccine of the present invention is manufactured by mixing an effective amount of an active ingredient together with one or more kinds of pharmacologically acceptable carriers, and employing any method well known in the art of pharmaceutics. Various substances are known as the pharmacologically acceptable carriers, and one appropriately selected from the substances is used. Examples thereof may include buffers and various additives such as salts, serum, albumin, and amino acids.

(Method for Improvement of Antibody Productivity of Vaccine)

A method for improvement of antibody productivity of a vaccine of the present invention includes administering NK cells (preferably activated NK cells) and a vaccine to a patient. It should be noted that the NK cells do not need to be NK cells derived from the patient.

However, the method preferably includes at least the following steps. It should be noted that that the order of the following steps (1) and (2) may be changed.

(1) a step of administering activated NK cells acquired from a patient to the patient
(2) a step of administering a vaccine to the patient (Vaccine)

The "vaccine" for which the agent for improvement of the present invention may be used is not particularly limited, and the agent may be used for a live vaccine, an inactivated vaccine, a peptide vaccine, a plasmid DNA vaccine, an antigen-antibody complex vaccine, or the like. A commercially available vaccine known per se may be used as the vaccine.

The agent for improvement of the present invention is used for preferably a hepatitis vaccine, more preferably a hepatitis B vaccine.

(Agent for Treatment of Hepatitis)

An agent for treatment of hepatitis of the present invention is an agent for treatment of hepatitis, containing at least a combination of NK cells as an active ingredient and a hepatitis vaccine as an active ingredient.

It should be noted that the agent for treatment of the present invention has such a form that the NK cells as the active ingredient and the hepatitis vaccine as the active ingredient can be administered to a patient at the same time or separately.

(Kit for Treatment of Hepatitis)

A kit for treatment of hepatitis of the present invention includes at least an agent for improvement of antibody productivity of a vaccine, containing NK cells as an active ingredient, and a hepatitis vaccine.

The kit of the present invention has such a form that the agent for improvement of antibody productivity and the hepatitis vaccine can be administered to a patient at the same time or separately.

(Method for Treatment of Hepatitis)

A method for treatment hepatitis of the present invention includes administering NK cells (preferably activated NK cells) and a hepatitis vaccine to a patient. It should be noted that the NK cells do not need to be NK cells derived from the patient.

However, the method preferably includes at least the following steps. It should be noted that the order of the following steps (1) and (2) may be changed.
(1) a step of administering activated NK cells acquired from a hepatitis patient to the patient
(2) a step of administering a hepatitis vaccine to the patient (Forms of Agent for Improvement of Antibody Productivity and Agent for Treatment of Hepatitis)

The agent for improvement of antibody productivity and agent for treatment of hepatitis of the present invention may be used in such forms that the agents are contained in drugs having dosage forms such as buffered solutions, capsules, granules, powders, and syrups to be orally administered to a living body, or may be used in such forms that the agents are contained in drugs having dosage forms such as injections, drops, and suppositories to be parenterally administered to a living body by subcutaneous injection, muscular injection, intravenous injection, and the like.

The agent for improvement of antibody productivity and agent for treatment of hepatitis of the present invention may be subjected to lyophilization, and may be used in such forms that the agents are contained in drugs together with various additives such as therapeutically acceptable carriers, pH buffers, stabilizers, and excipients.

The method for administration and dosage of the agent for improvement of antibody productivity and agent for treatment of hepatitis of the present invention are appropriately determined in association with processes of a preclinical trial and a clinical trial. In the case of orally administering the agent for improvement of antibody productivity and agent for treatment of hepatitis of the present invention, the dosage is generally about 0.01 mg to about 1,000 mg per day for an adult human (the concentration of the NK cells and/or activated NK cells contained falls within the range of generally about $1 \times 10^5$ to $1 \times 10^{11}$ cells/ml, preferably about $1 \times 10^6$ to $1.0 \times 10^{10}$ cells/ml), and such oral administration is performed once or in several divided portions. Further, in the case of parenterally administering the agent for improvement of antibody productivity and agent for treatment of hepatitis of the present invention, the dosage is generally about 0.01 mg to about 1,000 mg per administration for an adult human (the concentration of the NK cells and/or activated NK cells contained falls within the range of generally about $1 \times 10^5$ to $1 \times 10^{11}$ cells/ml, preferably about $1 \times 10^6$ to $1 \times 10^{10}$ cells/ml).

It should be noted that the dosage of a pharmaceutical composition through oral administration or parenteral administration is determined depending on the age, body weight, and disease symptoms.

(Subject)

The agent for inhibition of cancer development, agent for improvement of antibody productivity, agent for treatment of hepatitis, method for inhibition of cancer development, method for improvement of antibody productivity, and method for treatment of hepatitis of the present invention are applied to mammals including humans. Examples thereof include humans, dogs, cats, horses (in particular, horses for racing), and pigs.

Hereinafter, the present invention is more specifically described by way of Examples. It should be noted that Examples shown below are intended to describe the present invention, and the scope of the present invention is by no means limited thereto.

EXAMPLE 1

(Culture and Proliferation of NK Cells)

Activated NK cells were cultured and proliferated by culturing and proliferating autologous peripheral blood lymphocytes through the following steps.

(Step 1)

Solutions containing 0.1 µl/ml of Orthoclone OKT3 (anti-CD3 antibody available from Janssen Pharmaceutical K.K.) and 20 to 40 µl/ml of MABCAMPATH (anti-CD52 antibody available from Bayer) with respect to 20 ml of a phosphate buffer (PBS) were prepared.

(Step 2)

The solutions of Step 1 were dispensed into separate 225-cm$^2$ flasks and left to stand still at 4° C. overnight.

(Step 3)

The flasks of Step 2 were washed twice with PBS.

(Step 4)

30 ml of heparinized peripheral blood were collected from a healthy subject, and peripheral blood mononuclear cells (PBMCs) were separated by a density-gradient centrifugation method using Ficoll-Paque Plus (available from Amersham Pharmacia Biotech) as a medium.

(Step 5)

The PBMCs separated in Step 4 were suspended in an NKGM medium (available from Kohjin Bio Co., Ltd.) containing IL-2 (500 units/ml, Chiron) at a concentration of 0.5 to $1 \times 10^6$ cells/ml, and patient plasma was added at 2 to 10% to the suspension to prepare a culture medium. At this stage, the volume of the culture medium was 60 to 120 ml. The culture medium was added to the culture flasks subjected to antibody immobilization treatment obtained in Step 3. After that, the cells were cultured in a 5% $CO_2$ incubator under the environment of 37° C.

(Step 6)

After the confirmation of production of a large number of colonies and blastogenesis (blast formation) on days 3 to 5 after the start of the culture, a culture medium was added at 20 to 100%, and IL-2 was added at 500 units/ml. In general, this timing was day 3 after the start of the culture.

(Step 7)

On days 1 to 3 (day 1 in most cases) in the logarithmic phase after the addition of the culture medium in Step 6, a culture medium containing activated lymphocytes was injected into NKGM-B (1-L bag). In addition, the culture medium was dispensed into 2 or 3 bags. 100 to 300 ml of the NKGM medium and 100,000 to 200,000 units of IL-2 per bag were added at an interval of 3 or 4 days after the dispensation.

(Step 8)

On days 14 to 21 after the start of the culture, the culture medium was transferred from each of the bags to a centrifugation tube, followed by centrifugation at 600 G for 10 minutes. The supernatant was aspirated from the centrifugation tube so that the pellet was left. After that, PBS was added to the pellet for washing, and the centrifugation operation was performed again. This work was repeated 2 or 3 times to wash the cultured lymphocytes well. Finally, the pellet was harvested and suspended in 100 ml of physiological saline, and human serum albumin was added at 2 to 4% to the suspension. Finally, it was confirmed that the results of a sterility test and an endotoxin test were negative.

(Cryopreservation and Thawing)

On days 3 to 7 after the start of the culture, the cultured cells were washed, loaded into a tube for freezing together with a cryopreservative KM Banker (Kohjin Bio Co., Ltd.), and preserved in a liquid nitrogen tank kept at −190° C. or less. After thawing, the cells were cultured with an NKGM culture medium supplemented with IL-2 for 10 to 14 days.

(Analysis Results of Activated Lymphocytes in Culture Medium)

CXCR3 chemokine receptors NKG2D and TRAIL and specific activation receptors NKp30, NKp44, and NKp46 were found to be expressed on the surface of the cultured and proliferated NK cells. In addition, sustained IFNγ production was found in the cultured NK cells, confirming that the cytotoxicity directed against K562 was kept high at least until 3 weeks of the culture.

The above-mentioned results confirmed that the activated NK cells were present at a high concentration in the solution.

EXAMPLE 2

(Confirmation of Inhibition of Cancer Development by Activated NK Cell Administration)

Cultured lymphocytes containing activated NK cells obtained from a healthy subject were administered to the healthy subject. Then, rates of cancer development in the healthy subject to which the cultured lymphocytes were administered and a healthy subject to which the cultured lymphocytes were not administered were confirmed. The details are as described below.

(Administration of NK Cells)

The cultured lymphocytes of Example 1 were thawed and cultured in an NKGM culture medium supplemented with IL-2 for 10 to 14 days. Then, the cultured lymphocytes were washed and suspended in 100 ml of physiological saline, and the suspension was intravenously administered to a healthy subject by infusion.

Figure 1:
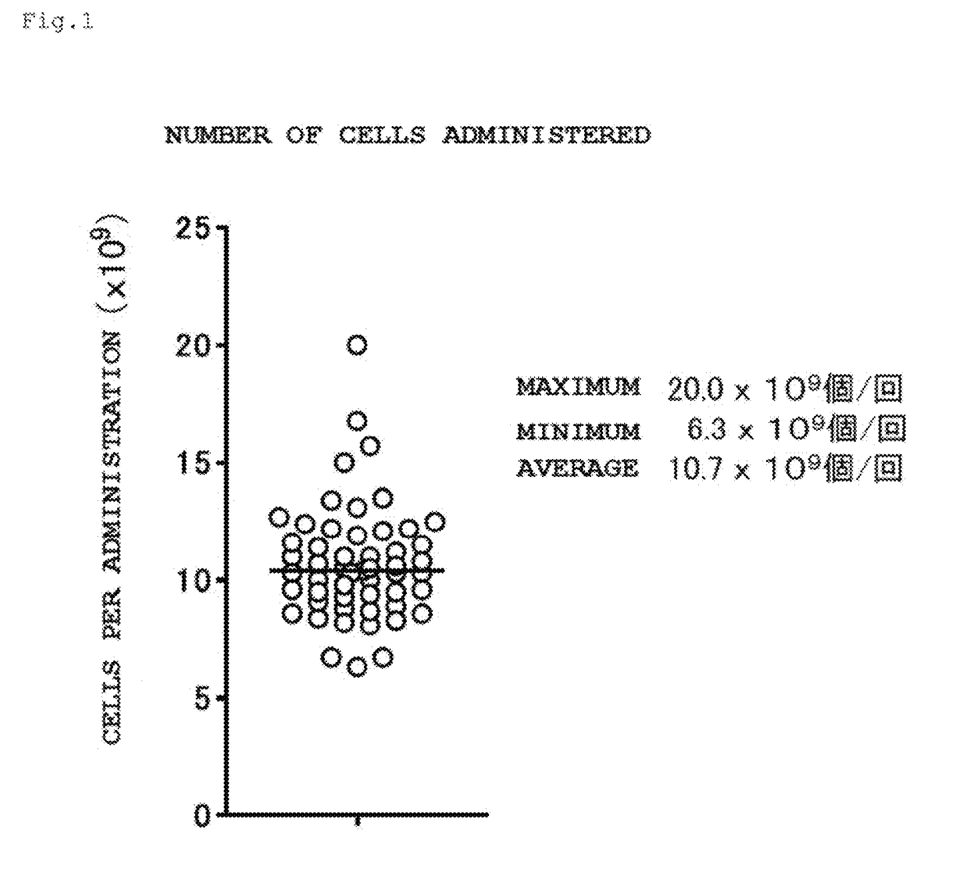
FIG. 1 shows measurement results of the number of NK cells administered (Example 2).
Figure 2:
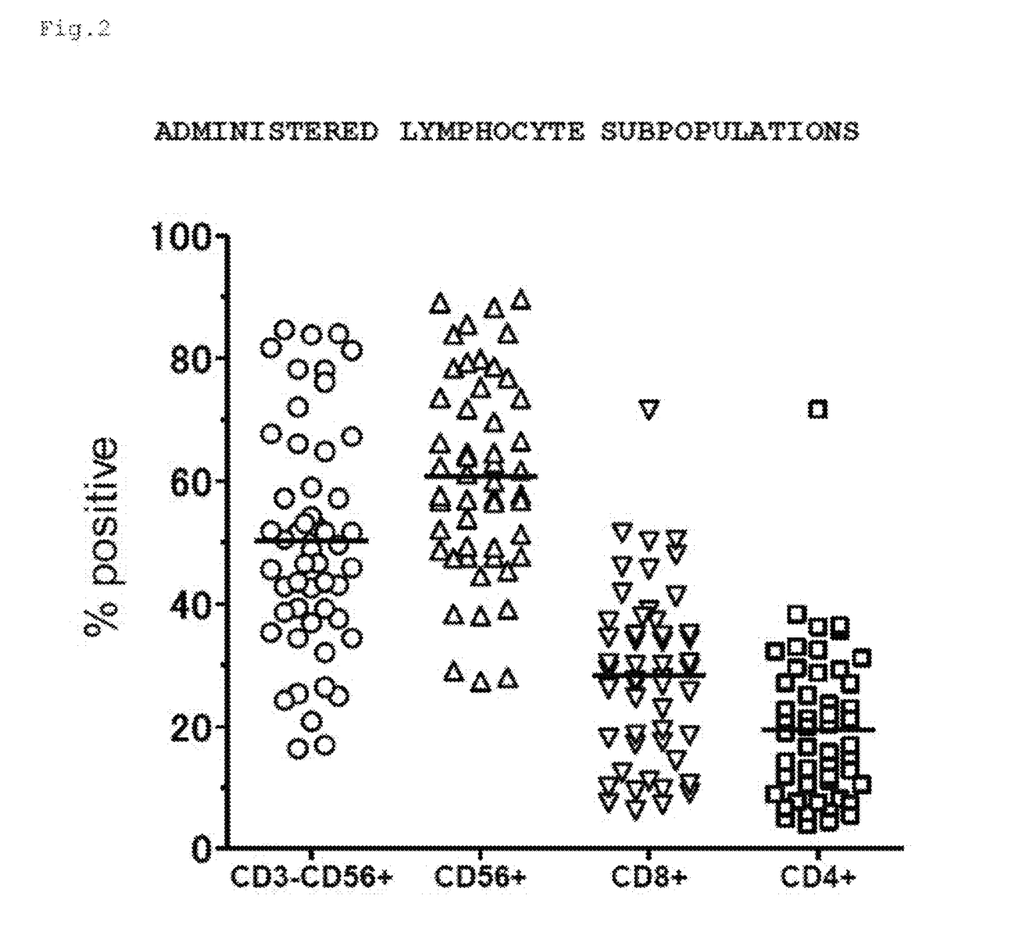
FIG. 2 shows analysis results of administered lymphocyte subpopulations (Example 2).

The number of the cultured autologous lymphocytes administered was $10.7 \times 10^9$ cells per administration (see: FIG. 1). In addition, CD3−CD56+ NK cells or CD56+ lymphocytes were contained in the largest amounts among the administered lymphocytes (FIG. 2).

It should be noted that the details of the administration are as described below.

(Healthy Subjects in NK Cell Administration and Non-Administration Groups)

NK cells were started to be cryopreserved in 2006 so that the cells were able to be administered 10 times or more for one healthy subject. 103 subjects whose NK cells were preserved for 13 months (minimum) or more until 2011 were adopted as test subjects. Of those, the "administration group," in which the administration was performed one or more times upon request from the subject in the preservation period, consisted of 53 subjects (31 males and 22 females), and the "non-administration group," in which there was no request for the administration, consisted of 50 subjects (25 males and 25 females). In the administration group, the administration was performed a total of 242 times, the number of times of administration per subject was 1 to 57, and the median was 3. A period to cancer development was defined as the number of months from the start of preservation to the cancer development.

(Profiles of Administration Group and Non-Administration Group)

Figure 3:
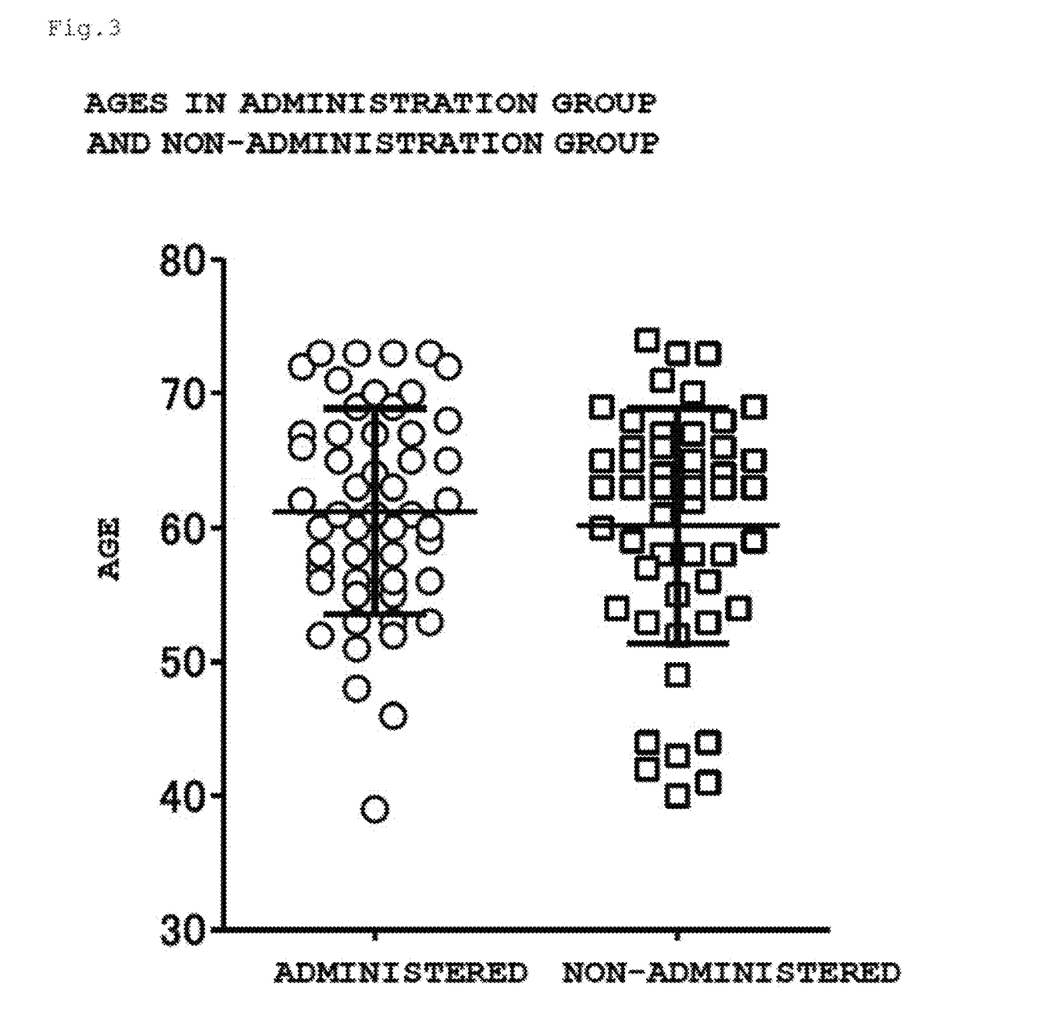
FIG. 3 shows profiles of ages in NK administration and non-administration groups (Example 2).
Figure 4:
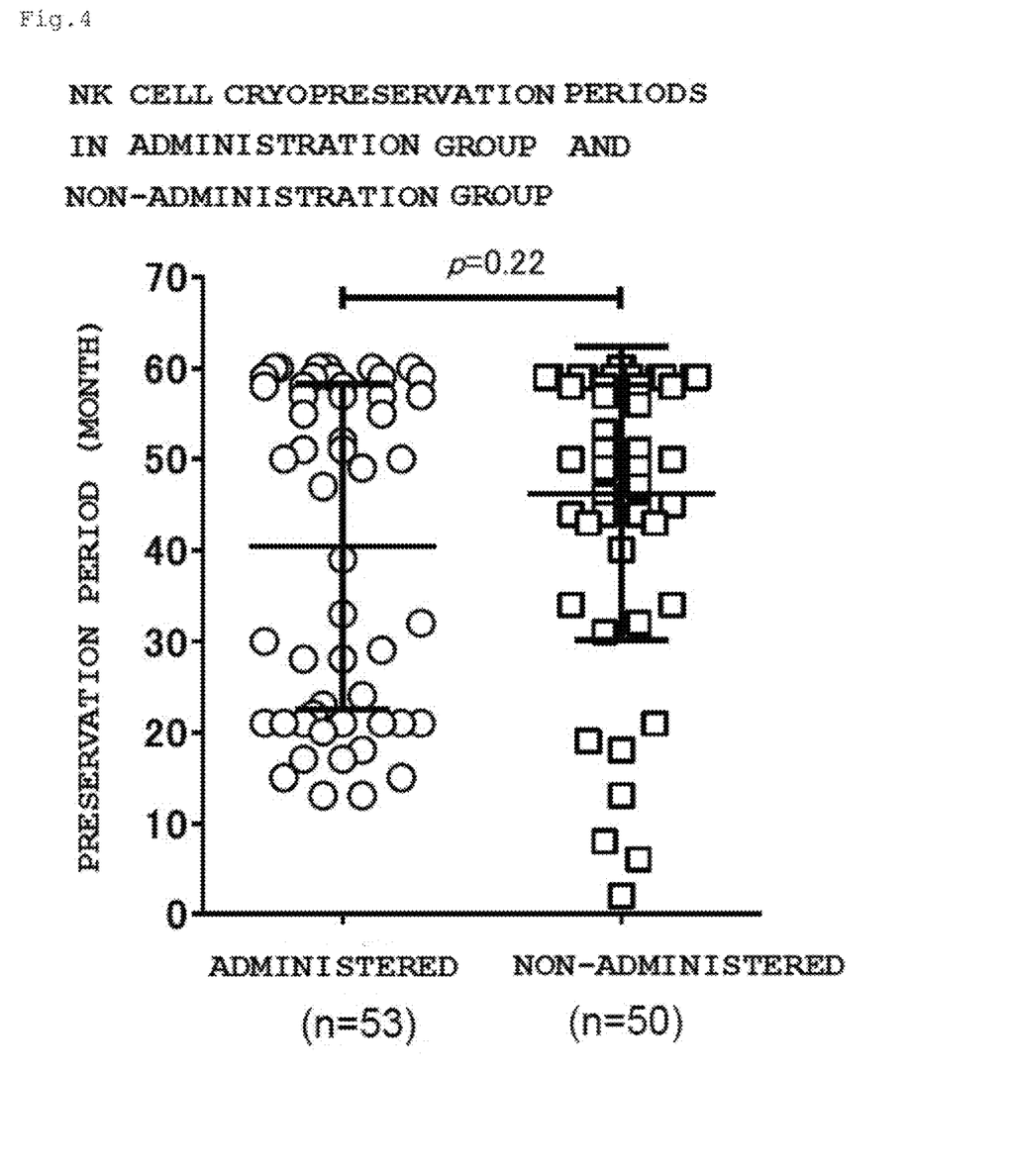
FIG. 4 shows NK cell cryopreservation periods in the NK cell administration and non-administration groups (Example 2).

There was no statistically significant difference in age (FIG. 3) and preservation period (FIG. 4) as profiles of all the subjects in both the groups. There was no difference in population between the administration group and the non-administration group. Hence, it was found that the inhibition of cancer development by NK cell administration was able to be statistically proven by a comparison between both the groups.

(Confirmation of Effect of Inhibiting Cancer Development in Administration Group)

Figure 5:
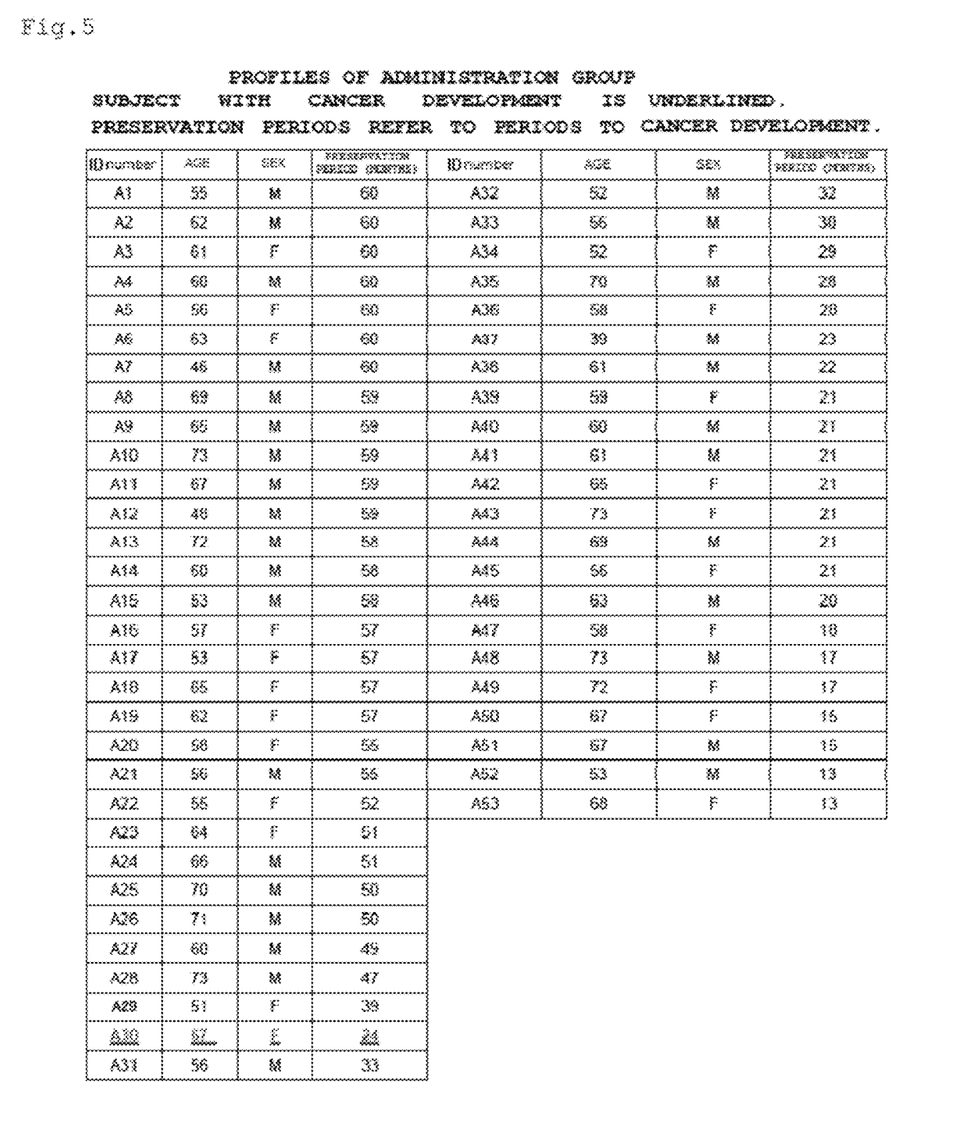
FIG. 5 shows profiles of healthy subjects in the NK cell administration group (Example 2).
Figure 6:
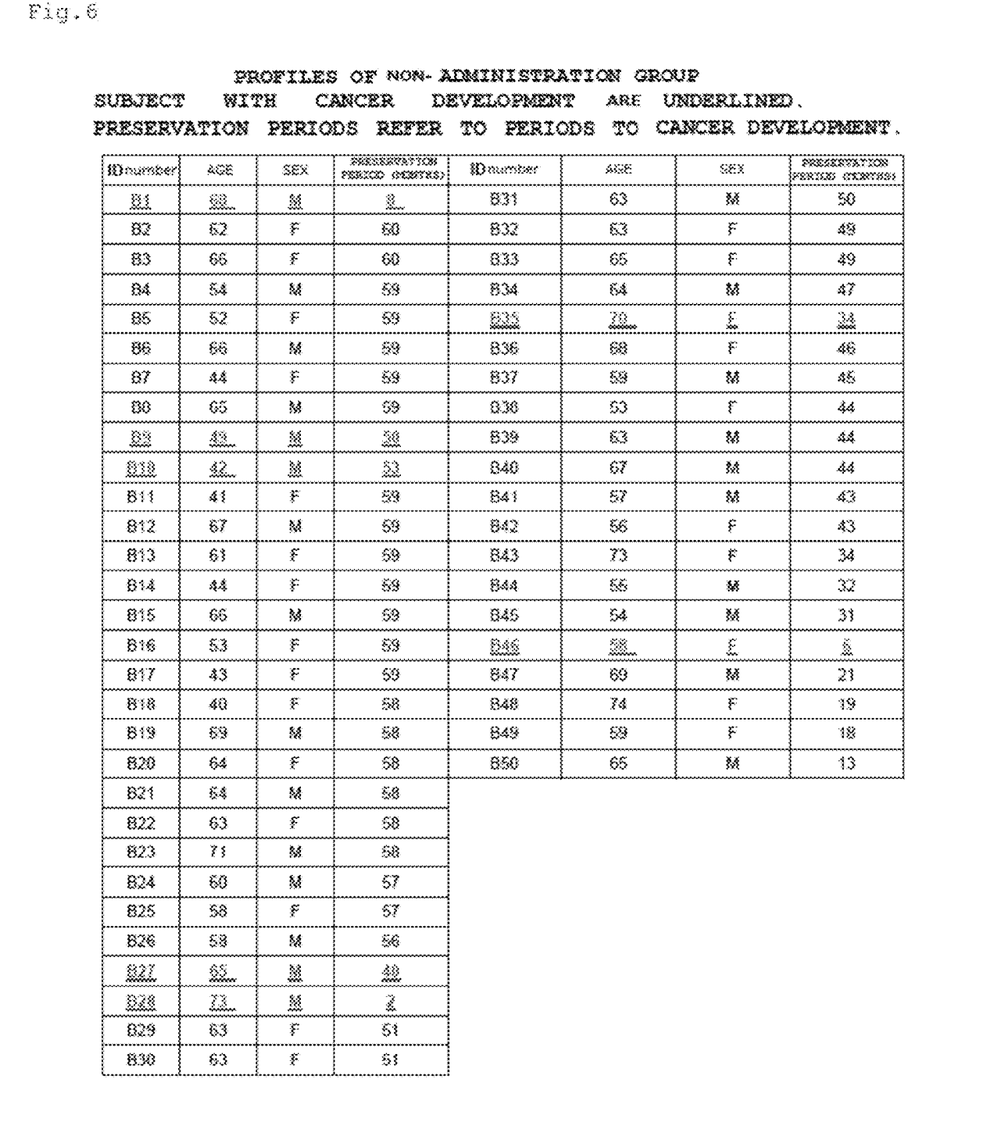
FIG. 6 shows profiles of healthy subjects in the NK cell non-administration group (Example 2).
Figure 7:
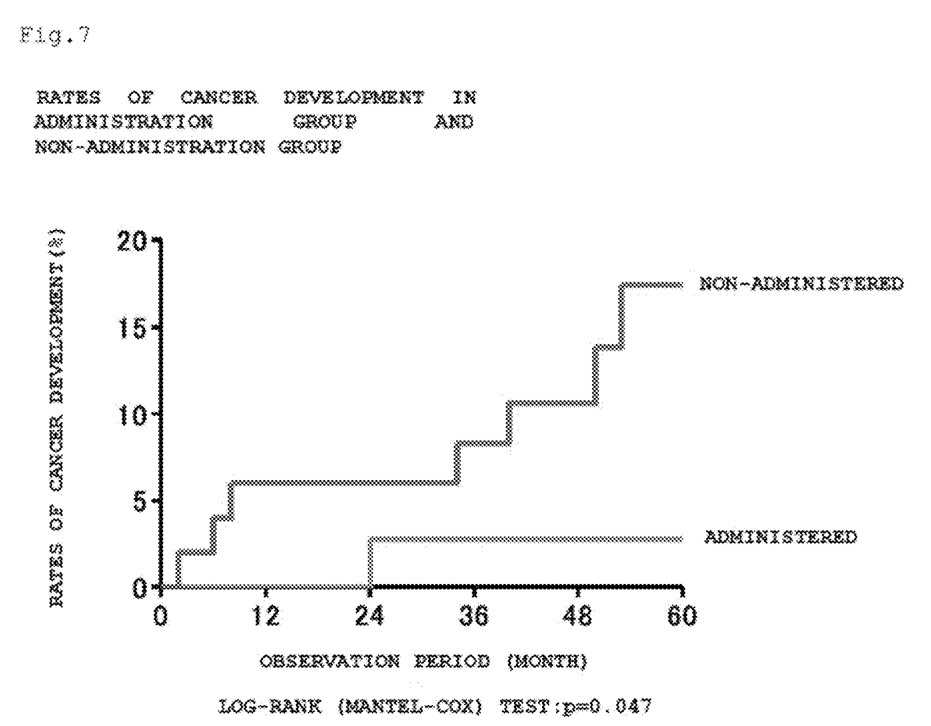
FIG. 7 shows results of rates of cancer development in the NK cell administration and non-administration groups (Example 2).

One subject in the "administration group" and seven subjects in the "non-administration group" were diagnosed to have cancer in the preservation period (Table 2, FIG. 5, and FIG. 6). A log-rank test was performed based on an incidence curve with the preservation period on the abscissa axis (FIG. 7). The results show that there was a significant difference in rate of cancer development between both the groups, and its relative risk was 0.24, indicating that cancer development was inhibited by 76% by the administration.

TABLE 2

Sites of cancer development and preservation periods to development

| | ID Number | Site | Preservation period (month) |
|---|---|---|---|
| Administration group | A30 | Breast cancer | 24 |
| Non-administration group | B1 | Lung cancer | 8 |
| | B9 | Colon cancer | 50 |
| | B10 | Pancreatic cancer | 53 |
| | B27 | Prostate cancer | 40 |
| | B28 | Prostate cancer | 2 |
| | B35 | Colon cancer | 34 |
| | B46 | Breast cancer | 6 |

(Inhibition of Cancer Development by NK Cell Administration and Comparison to Other Cancer Prevention Methods)

Figure 8:
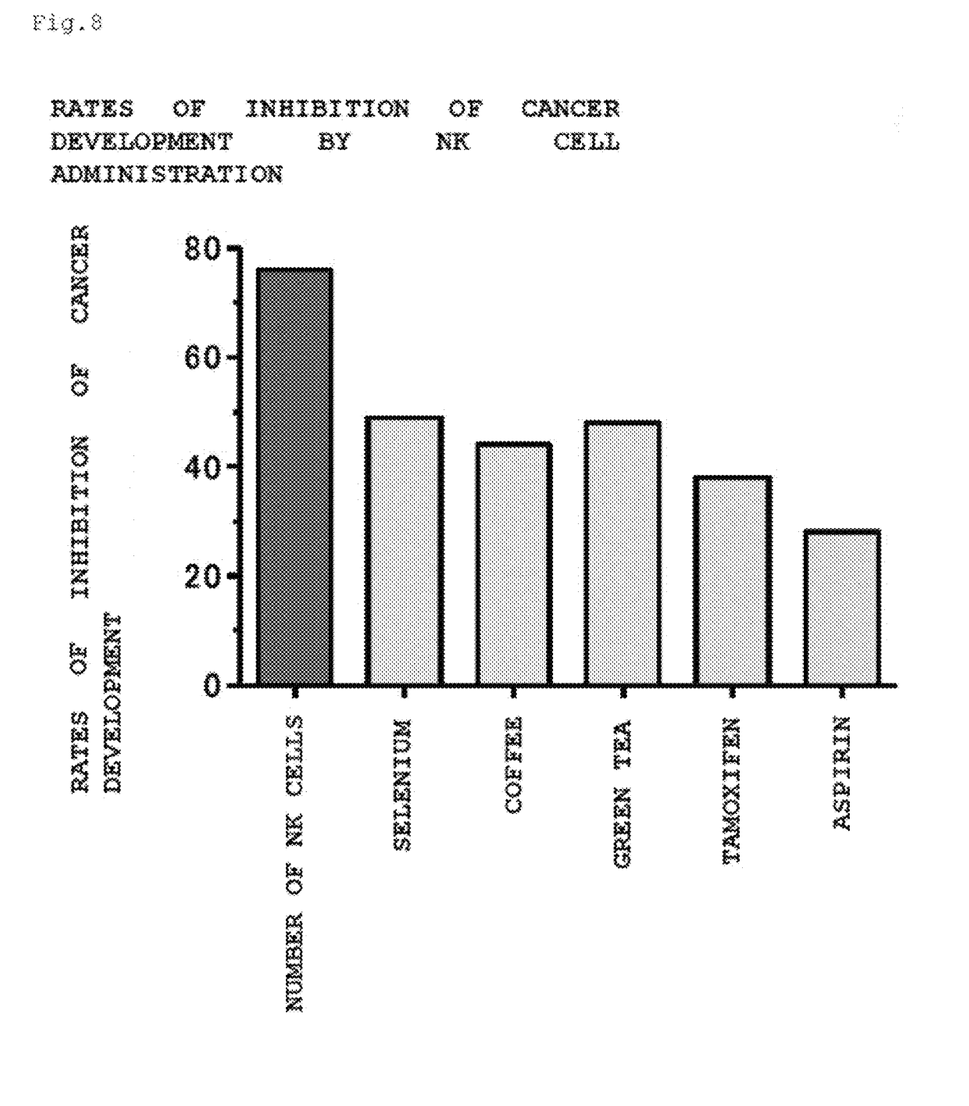
FIG. 8 shows results of various rates of inhibition of cancer development (Example 2).

Table 3 and FIG. 8 show cancer development-inhibiting effects of selenium (BJU Int. 2003; 91: 608), coffee (Nutr. Cancer 2010; 62: 21), green tea (Am. J. Epidemiol. 2008; 167: 71), tamoxifen (Lancet 2003; 361: 296), raloxifene (JAMA. 1999; 281: 2189), and aspirin (J. Natl. Cancer Inst. 2009; 101: 256), which are the previously reported cancer prevention methods, and the present invention. The cancer development-inhibiting effect of the present invention was an excellent effect as compared to those of the other methods.

TABLE 3

Relative risks of various cancer prevention methods

| Cancer prevention method | Type of cancer | Relative risk | Literature |
|---|---|---|---|
| selenium | Prostate cancer | 0.51 | BJU Int. 2003; 91: 608 |
| coffee | Smoker, advanced colon cancer | 0.56 | Nutr. Cancer 2010; 62: 21 |
| Green tea | Advanced prostate cancer | 0.52 | Am. J. Epidemiol. 2008; 167: 71 |
| Tamoxifen | All breast cancers | 0.62 | Lancet 2003; 361: 296 |
| Aspirin | Colorectal cancer | 0.72 | J. Natl. Cancer Inst. 2009; 101: 256 |
| Present invention | Cancer | 0.25 | |

EXAMPLE 3

(Confirmation of Increase in Antibody Titer by Activated NK Cell Administration)

Activated NK cells derived from five healthy subjects (A to E) and an HB vaccine were administered to the subjects themselves 1 to 3 times to confirm increases in antibody titer.

As a control, "activated T lymphocytes in which NK cells were not proliferated in large amounts" derived from healthy subjects (F to H) and an HB vaccine were administered to the subjects themselves to confirm increases in antibody titer.

It should be noted that a method for culture and proliferation of the activated T lymphocytes in which NK cells were not proliferated in large amounts is as described below.

(Method for Culture and Proliferation of Activated T Lymphocytes)

Peripheral blood lymphocytes were cultured and proliferated in order to obtain autologous activated T lymphocytes through the following steps.

(Step 1)

Solutions containing, in the case of culture of activated T cells, 5 μl/ml of an anti-CD3 antibody (Orthoclone OKT3 available from Janssen Pharmaceutical K.K.) with respect to 20 ml of a phosphate buffer (PBS) were prepared.

(Step 2)

The solutions of Step 1 were dispensed into separate 225-cm$^2$ flasks and left to stand still at 4° C. overnight.

(Step 3)

The flasks of Step 2 were washed twice with PBS.

(Step 4)

30 ml of heparinized peripheral blood were collected from the healthy subjects (F to H), and peripheral blood mononuclear cells (PBMCs) were separated by a density-gradient centrifugation method using Ficoll-Paque Plus (available from Amersham Pharmacia Biotech) as a medium.

(Step 5)

The PBMCs separated in Step 4 were suspended in an NKGM medium (available from Kohjin Bio Co., Ltd.) containing IL-2 (500 units/ml, Chiron) at a concentration of 0.5 to $1\times10^6$ cells/ml, and patient plasma was added at 2 to 10% to the suspension to prepare a culture medium. At this stage, the volume of the culture medium was 60 to 120 ml. The culture medium was added to the culture flasks subjected to antibody immobilization treatment of Step 3. After that, the cells were cultured in a 5% $CO_2$ incubator under the environment of 37° C.

(Step 6)

After the confirmation of production of a large number of colonies and blastogenesis (blast formation) on days 3 to 5 after the start of the culture, a culture medium was further added at 20 to 100%, and IL-2 was added at 500 units/ml. In general, this timing was day 3 after the start of the culture.

(Step 7)

On days 1 to 3 (day 1 in most cases) in the logarithmic phase after the addition of the culture medium in Step 6, a culture medium containing activated lymphocytes was injected into NKGM-B (1-L bag). In general, the culture medium was dispensed into 2 or 3 bags. 100 to 300 ml of the NKGM medium and 100,000 to 200,000 units of IL-2 per bag were added at an interval of 3 or 4 days after the dispensation.

(Step 8)

On days 14 to 21 after the start of the culture, the culture medium was transferred from each of the bags to a centrifugation tube, followed by centrifugation at 600 G for 10 minutes. The supernatant was aspirated from the centrifugation tube so that the pellet was left. After that, PBS was added to the pellet for washing, and the centrifugation operation was performed again. This work was repeated 2 or 3 times to wash the cultured lymphocytes well. Finally, the pellet was harvested and suspended in 100 ml of physiological saline, and human serum albumin was added at 2 to 4% to the suspension. Finally, it was confirmed that the results of a sterility test and an endotoxin test were negative.

(Procedures for Administrating Cultured Activated NK Cells or T Cells and Administrating Hepatitis B Vaccine)

In the NK cell administration group, autologous cultured activated NK cells were administered to five healthy subjects (A to E) from the cubital vein. 3 days after the administration, 0.5 ml of a genetically-modified HB vaccine (Bimmugen, Kaketsuken) was intramuscularly injected. 4 weeks after the administration of the vaccine, an HBs antibody titer was investigated. Based on this combination, after the first administration, the second administration was performed 6 weeks later and the third administration was performed 6 months later. It should be noted that the administration was performed only once for the subjects A and C.

It should be noted that, in the T lymphocyte administration group as a control, "cultured activated T lymphocytes not containing NK cells in large amounts" were intravenously injected to three healthy subjects (F to H) themselves, and an HB vaccine was further administered to the subjects themselves. The administration was performed at the same interval as that in the NK cell administration group.

(Measurement of Number of NK Cells)

The cultured lymphocytes containing NK cells (suspended in physiological saline) obtained in Example 1 and the above-mentioned lymphocytes suspended in physiological saline were each placed in an Eppendorf tube, a predetermined labeled antibody was added to the tube, and the cells were stained by an ordinary method. The stained cells were immediately analyzed by flow cytometry to measure the number of $CD3^-CD56^+$ NK cells.

(Measurement Results of Number of NK Cells)

Figure 9:
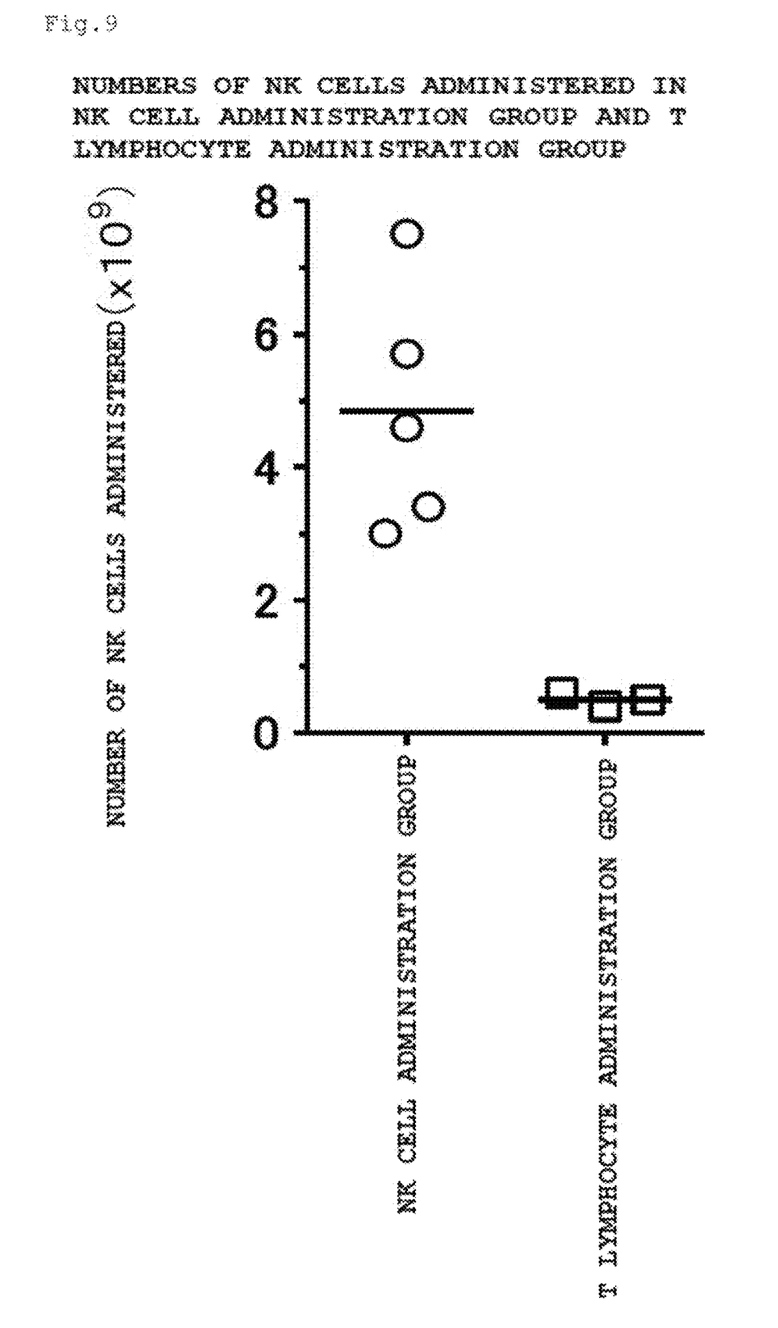
FIG. 9 shows a comparison between the numbers of NK cells administered in an NK cell administration group and a T lymphocyte administration group (Example 3).

FIG. 9 shows average values of the numbers of NK cells in the cultured lymphocytes containing NK cells obtained in Example 1 and the above-mentioned lymphocytes suspended in physiological saline.

FIG. 9 is a plot of average values of the numbers of the NK cells administered in each case. The number of the NK cells administered was $4.8\times10^9$ cells on average in the NK cell administration group (A to E), and was $0.5\times10^9$ cells on average in the T lymphocyte administration group (F to H). This revealed that the number of the NK cells administered in the NK cell administration group was about 10 times as large as that in the T lymphocyte administration group.

(Method for Measurement of HBs Antibody Titer)

HBs antibody titers in blood acquired from the healthy subjects A to H before or after the above-mentioned administration were measured by chemiluminescent immunoassay (CLIA) known per se use. A normal value in this method is less than 10.0 mIU/ml.

(Measurement Results of HBs Antibody Titer)

Figure 10:
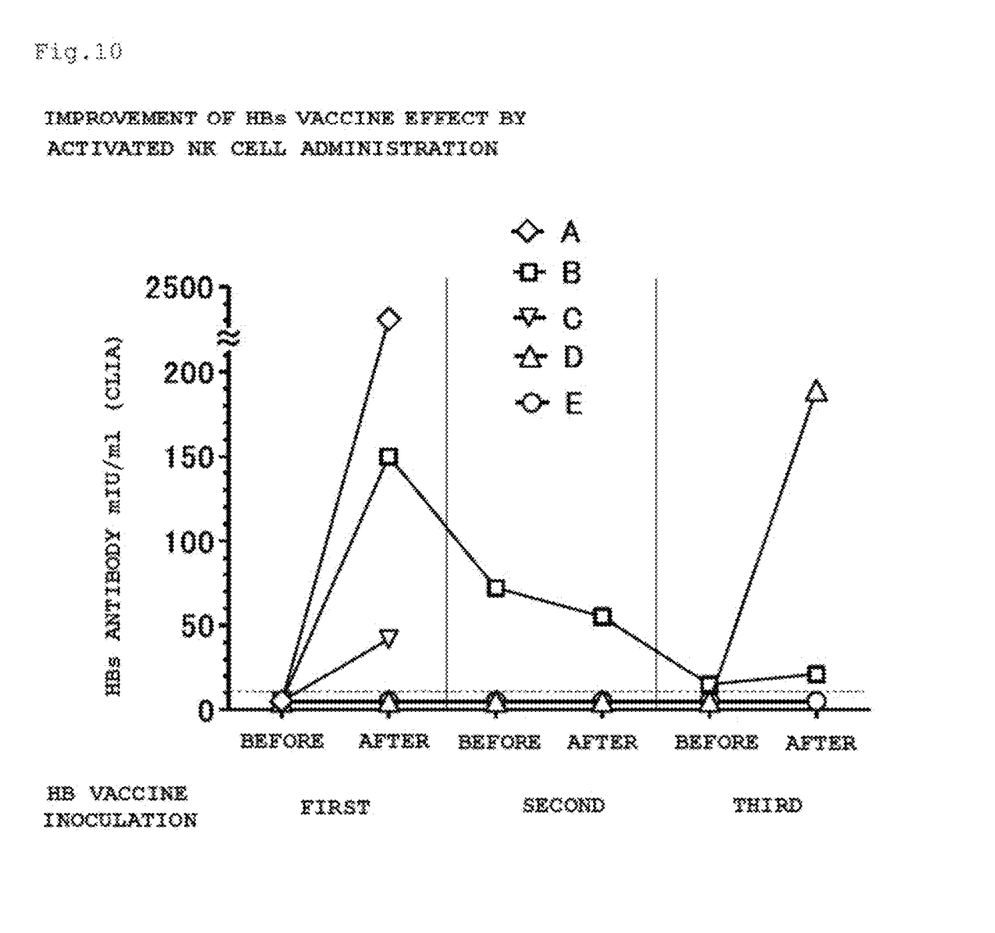
FIG. 10 shows results of improvement of an HBs vaccine effect by activated NK cell administration (Example 3).
Figure 11:
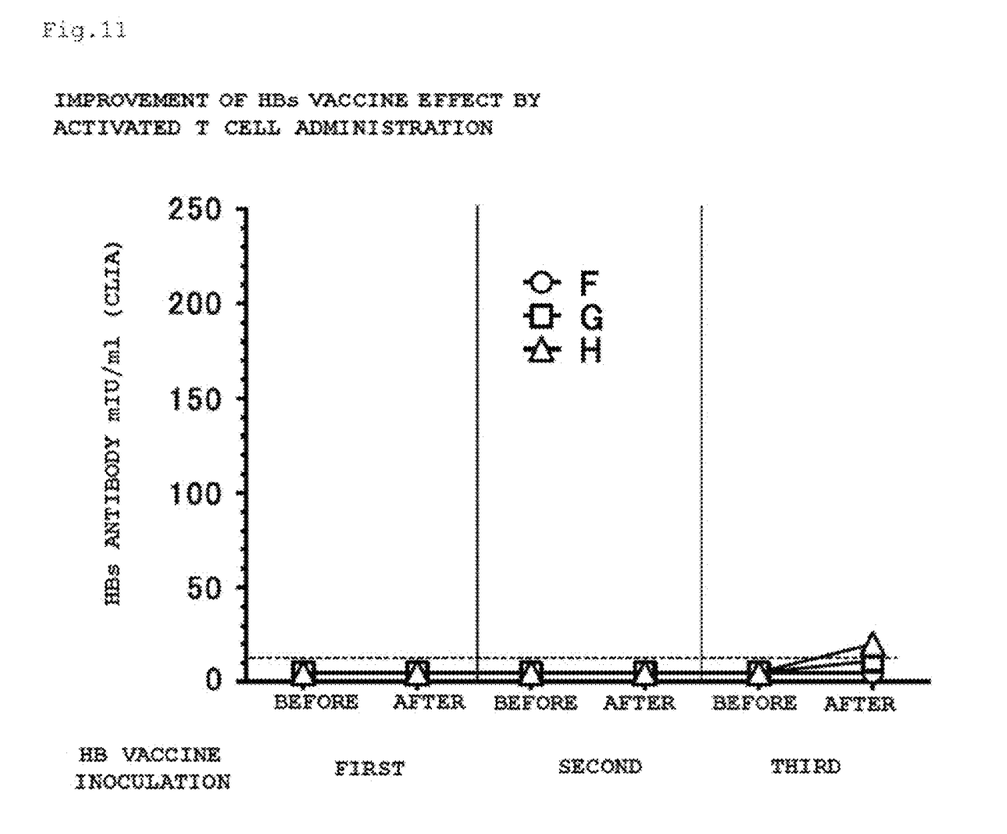
FIG. 11 shows results of improvement of an HBs vaccine effect by activated T cell administration (Example 3).

FIG. 10 and FIG. 11 show HBs antibody titers in blood acquired from the healthy subjects A to H. In the four (80%: four subjects A, B, C, and D) out of five subjects, significantly high antibody titers were able to be induced (see: FIG. 10).

On the other hand, in the control, i.e., the administration of activated T lymphocytes (the number of the NK cells administered was less than 100,000,000) and the hepatitis B vaccine, no clear increase in antibody titer was found (see: FIG. 11).

As described above, the increase in antibody titer was able to be achieved by administering the NK cells and the hepatitis B vaccine. Particularly when the fact that the healthy subjects A to D were males aged 60 or more hardly showing increases in antibody titer was taken into consideration as well, the present invention showed an extremely excellent antibody titer-increasing effect.

Conclusion

The results of Example 3 suggest that hepatitis can be treated by administering the NK cells and the hepatitis vaccine to a patient.

INDUSTRIAL APPLICABILITY

In the present invention, the novel agent for inhibition of cancer development and agent for improvement of antibody productivity were able to be provided.

The invention claimed is:

1. A method for increasing antibody productivity of a hepatitis B vaccine in a patient, comprising the following steps (1) and (2) or (1)' and (2)':
   (1) a step of administering an activated autologous NK cell to a patient, the activated autologous NK cell derived from the patient; and
   (2) a step of administering a hepatitis B vaccine to the patient; or
   (1)' a step of administering a hepatitis B vaccine to a patient; and
   (2)' a step of administering an activated autologous NK cell to the patient, the activated autologous NK cell derived from the patient, wherein the method results in an increased antibody productivity of the hepatitis B vaccine in the patient comprising an increased antibody titer against the hepatitis B vaccine.

2. A method for treatment of hepatitis B, comprising the following steps (1) and (2) or (1)' and (2)':
   (1) a step of administering an activated autologous NK cell to a patient, the activated autologous NK cell derived from the patient; and
   (2) a step of administering a hepatitis B vaccine to the patient; or
   (1)' a step of administering a hepatitis B vaccine to a patient; and
   (2)' a step of administering an activated autologous NK cell to the patient, the activated autologous NK cell derived from the patient, wherein the method results in an increased antibody productivity of the hepatitis B vaccine in the patient comprising an increased antibody titer against the hepatitis B vaccine.

3. A method for increasing antibody productivity according to claim 1, wherein the patient is 60 years old or more.

4. A method for increasing antibody productivity according to claim 3 wherein the patient is male.

* * * * *